United States Patent [19]

Suzuki et al.

[11] Patent Number: 5,096,613
[45] Date of Patent: Mar. 17, 1992

[54] OPTICALLY ACTIVE FLUORINE-CONTAINING ALCOHOL COMPOUNDS AND LIQUID CRYSTAL COMPOUNDS THEREFROM

[75] Inventors: Yoshiichi Suzuki; Yasunori Sadamune; Noriko Yamakawa, all of Tokyo, Japan

[73] Assignee: Showa Shell Sekiyu Kabushiki Kaisha, Tokyo, Japan

[21] Appl. No.: 572,215

[22] Filed: Aug. 24, 1990

[30] Foreign Application Priority Data

Aug. 28, 1989 [JP] Japan .................... 1-220658

[51] Int. Cl.$^5$ .............. C09K 19/12; C09K 19/20; C07C 69/76
[52] U.S. Cl. ............ 252/299.65; 252/299.64; 252/299.01; 252/299.6; 252/299.67; 252/299.66; 560/8; 560/55; 560/59; 560/60; 560/61; 560/64; 560/73; 560/76; 560/102; 359/103
[58] Field of Search ........... 252/299.01, 299.6, 299.61, 252/299.62, 299.63, 299.64, 299.65, 299.66, 299.67; 560/8, 55, 59, 60, 61, 64, 73, 76, 102; 350/350 R, 350 S

[56] References Cited

U.S. PATENT DOCUMENTS

| | | | |
|---|---|---|---|
| 4,886,619 | 12/1989 | Janulis | 252/299.1 |
| 4,917,817 | 4/1990 | Nohira et al. | 252/299.01 |
| 4,918,213 | 4/1990 | Nohira et al. | 558/271 |
| 4,921,632 | 5/1990 | Nakamura et al. | 252/299.1 |

FOREIGN PATENT DOCUMENTS

| | | | |
|---|---|---|---|
| 62-174046 | 7/1987 | Japan | 252/299.6 |
| 62-198647 | 9/1987 | Japan | 252/299.6 |
| 63-44551 | 2/1988 | Japan | 252/299.6 |
| 63-243062 | 10/1988 | Japan | 252/299.6 |
| 64-3154 | 1/1989 | Japan | 252/299.6 |
| 64-22839 | 1/1989 | Japan | 252/299.6 |
| 64-26536 | 1/1989 | Japan | 252/299.6 |
| 64-75455 | 3/1989 | Japan | 252/299.6 |
| 64-75456 | 3/1989 | Japan | 252/299.6 |

OTHER PUBLICATIONS

Demus, D. et al., Eds. Flüssige Kristalle in Tabellen II, VEB, Leipzig, 1984, p. 118.

Primary Examiner—John S. Maples
Assistant Examiner—Shean C. Wu
Attorney, Agent, or Firm—Cushman, Darby & Cushman

[57] ABSTRACT

An optically active fluorine-containing alcohol of $$HO-(CH_2)_n-\overset{*}{\underset{|}{C}}H-O-R_2 \quad \text{with } CF_3 \text{ on carbon} \qquad (I)$$

where $R_2$ is a $C_{1-18}$ alkyl and n is 2–10, and liquid crystal compound of $$R_1-(X)_p-(A)-Y-(B)-Z-CH_2-CH_2-\overset{*}{\underset{|}{C}}H-O-R_2 \quad \text{with } CF_3 \qquad (II)$$

wherein $R_1$ and $R_2$ each is a $C_{1-18}$ alkyl, X is O, COO or OCO, Y is COO, OCO, $CH_2O$ or $OCH_2$, Z is COO or O, (A) and (B) each is for example

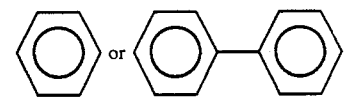

and p is zero or one, which is prepared from (I) above.

2 Claims, 1 Drawing Sheet

OPTICALLY ACTIVE FLUORINE-CONTAINING ALCOHOL COMPOUNDS AND LIQUID CRYSTAL COMPOUNDS THEREFROM

The present invention relates to a novel optically active fluorine-containing alcohol compound which is useful as an intermediate for producing a liquid crystal compound. The present invention relates also to a novel fluorine-containing liquid crystal compound, prepared from the alcohol compound.

Series of fluorine-containing liquid crystal compound have been patented (JP 63-307837, JP 64-3154) in the literature. Optically active alcohols for preparing the fluorine-containing liquid crystal compounds mentioned in JP 63-307837 are 1-trifluoromethyl heptanol, 1-trifluoromethyl nonyl alcohol, β-trifluoro-methyl-8-phenethyl alcohol, 1-trifluoromethyl-3-phenyl propanol, 1-phenyl-2-monofluoroethyl alcohol, 1-difluoromethylpentanol, 1-difluoronethylnonyl alcohol whereas optically active fluorine-containing liquid crystal compounds mentioned in JP 64-3154 are

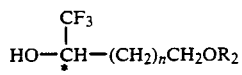

or

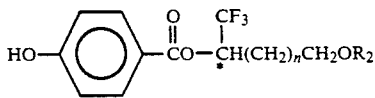

However, in the present invention novel optically active fluorine-containing alcohols which have an ether linkage on one end of an asymmetric carbon which is substituted by trifluoromethyl group, are mentioned. The present invention is also focussed to a novel fluorine-containing liquid crystal compounds synthesized from the novel optically active fluorine-containing alcohol. One of the general structure of optically active compounds having the formula (I) is shown below.

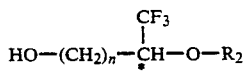

where $R_2$ is a $C_{1-18}$ alkyl group and n is from 2 to 10 and * shows an asymmetric carbon.

Liquid crystal compounds (II) prepared from the (I) have the general structural formula shown below:

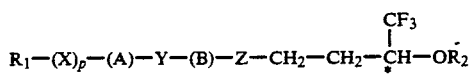

where $R_1$ and $R_2$ each is a $C_{1-18}$ alkyl group, X is O,

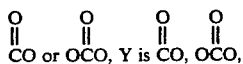

CO or OCO, Y is CO, OCO, $CH_2O$ or $OCH_2$, Z is

or O, (A) and (B) each is a cyclic group selected from

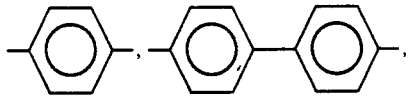

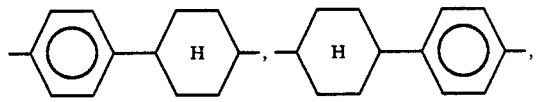

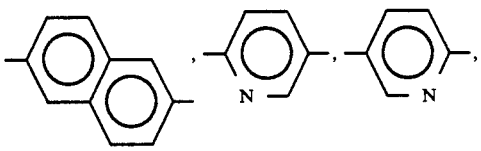

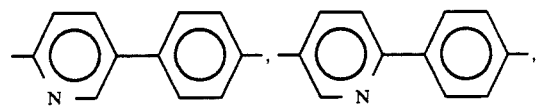

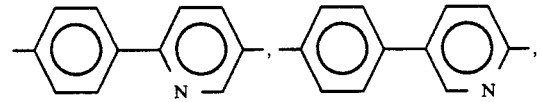

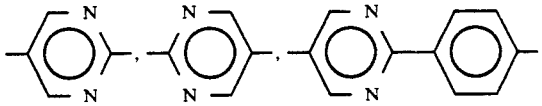

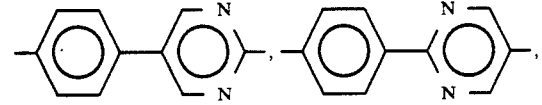

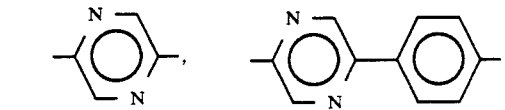

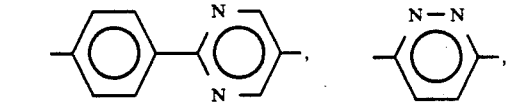

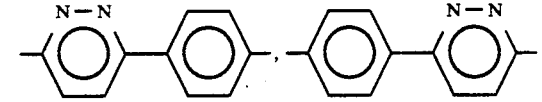

where one or two of the hydrogen atoms may be substituted by a halogen atom, preferably a fluorine or chlorine atom, more preferably a fluorine atom and p is zero or one.

Typical compounds of the formula (I) are 4,4,4-trifluoro-3-methyloxybutanol, 4,4,4-trifluoro-3-ethyloxybutanol, 4,4,4-trifluoro-3-propyloxybutanol, 4,4,4-trifluoro-3-butoxybutanol, 4,4,4-trifluoro-3-pentyloxybutanol, 4,4,4 trifluoro-3-hexyloxybutanol, 4,4,4-trifluoro-3-heptyloxybutanol, 4,4,4-trifluoro-3-octyloxybutanol, 4,4,4-trifluoro-3-nonyloxybutanol, 4,4,4-trifluoro-3-decyloxybutanol, 4,4,4-trifluoro-3-undecyloxybutanol and 4,4,4-trifluoro-3-dodecyloxybutanol. In addition, the corresponding compounds of pentanol, hexanol, heptanol and octanol other than butanol derivatives may be mentioned.

Examples of the liquid crystal compounds of the formula (II) are 4,4,4-trifluoro-3-methyloxybutyloxycarbonylphenyl 4-alkyloxybiphenyl-4'-carboxylate, 4,4,4-trifluoro-3-ethyloxybutyloxycarbonyphenyl 4-alkyloxybiphenyl-4'-carboxylate, 4,4,4-trifluoro-3-propyloxybutyloxycarbonylphenyl 4-alkyloxybiphenyl-4'-carboxylate, 4,4,4-trifluoro-3-butyloxybutyloxycarbonylphenyl 4-alkyloxybiphenyl-4'-carboxylate, 4,4,4-trifluoro-3-pentyloxybutyloxycarbonylphenyl 4-alkyloxybiphenyl-4'-carboxylate, 4,4,4-trifluoro-3-hexyloxybutyloxycarbonylphenyl 4-alkyloxybiphenyl-4'-carboxylate, 4,4,4-trifluoro-3-heptyloxybutyloxycarbonylphenyl 4-alkyloxybiphenyl-4'-carboxylate, 4,4,4-trifluoro-3-octyloxybutyloxycarbonylphenyl 4-alkyloxybiphenyl-4'-carboxylate, 4,4,4-trifluoro-3-nonyloxybutyloxycarbonylphenyl 4-alkyloxybiphenyl-4'-carboxylate, 4,4,4-trifluoro-3-decyloxybutyloxycarbonylphenyl 4-alkyloxybiphenyl-4'-carboxylate, 4,4,4-trifluoro-3-undecyloxybutyloxycarbonylphenyl 4-alkyloxybiphenyl-4'-carboxylate, and 4,4,4-trifluoro-3-dodecyloxybutyloxycarbonylphenyl 4-alkyloxybiphenyl-4'-carboxylate. The corresponding compounds of pentyl esters, hexyl esters, heptyl esters and octyl esters to the butyl esters above may be mentioned.

There are (R) isomers and (S) isomers in the optically active compounds (I) and liquid crystal compounds (II). Preferable compounds are those having higher optical purity.

BRIEF DESCRIPTION OF THE DRAWING

The accompanying drawing shows IR spectrum of 4,4,4-trifluoro-3-hexyloxybutyloxycarbonylphenyl 4-octyloxybiphenyl-4'-carboxylate which is prepared by Example 2 mentioned below.

The optically active fluorine-containing alcohols of the formula (I) are prepared, for example, by allowing alkyl esters of (R)—(+)— or (S)—(—)—4,4,4-trifluoro-3-hydroxy alkanoic acid to react with alkyl halides in DMF solvent in the presence of a catalyst, for example, silver oxide to obtain alkyl ester of (R)—(+)— or (S)—(—)—4,4,4-trifluoro-3-alkyloxyalkanoic acid and reducing the ester in THF solvent in the presence of a reducing agent, for example, aluminium lithium hydride until (R)—(+)— or (S)—(—)—4,4,4-trifluoro-3-alkoxyalkanol is obtained. Butanol compounds are obtained when the alkanoic acid is butanoic acid. Similarly, pentanol, hexanol, heptanol or oxtanol compounds are prepared when pentanoic acid, hexanoic acid, heptanoic acid or octanoic acid is used in place of the butanoic acid, respectively.

Figure 1:
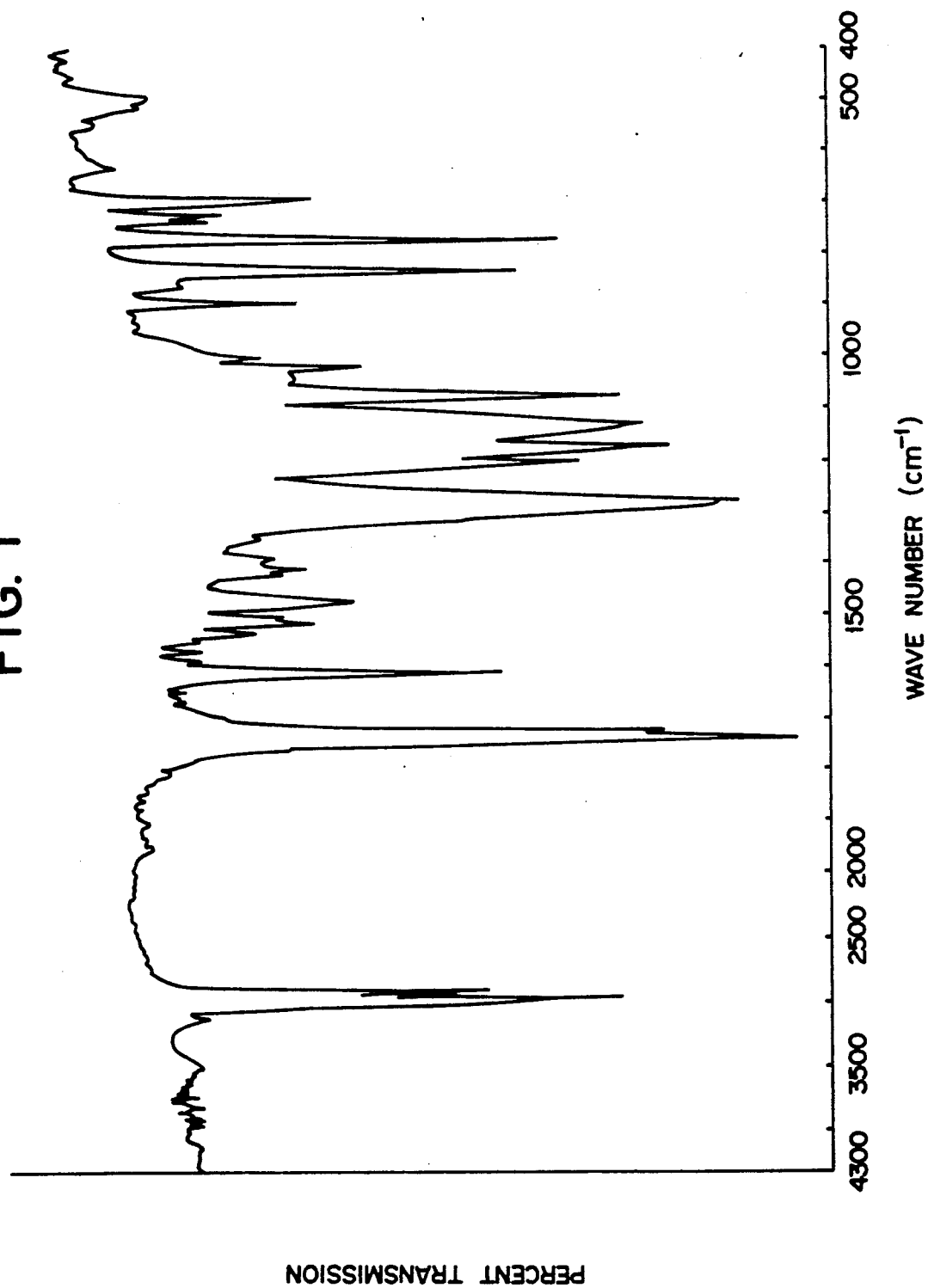

Reaction scheme is as follows when, for instance, butanoic acid is used:

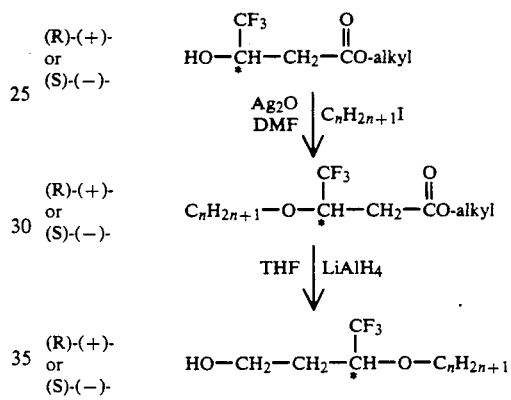

Preparation scheme of the liquid crystal compounds (II) is, for instance,

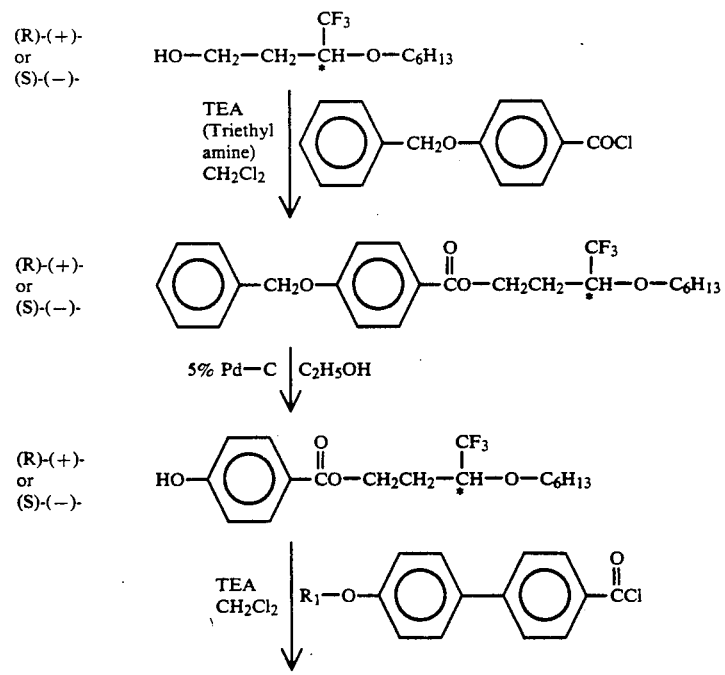

(R)-(+)- or (S)-(−)-  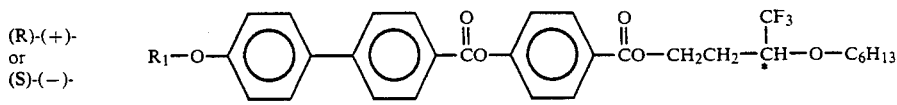

The present optically active fluorine-containing alcohol (I) is an intermediate useful for preparing a liquid crystal compound, particularly a ferro-electric liquid crystal.

The present liquid crystal compound (II) is ferro-electric of bistable state or binary bistable state which shows a usual SmC* phase and electroclinic effect at an $S_A$ phase. The compound (II) is used for electrooptical devices, liquid crystal optical devices and other liquid crystal devices.

EXAMPLE 1

(1) Synthesis of ethyl 4,4,4-trifuoro-3-hexyloxybutylate

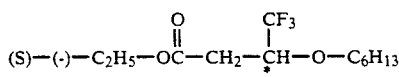

A solution of ethyl (S)—(−)—4,4,4-trifluoro-3-hydroxybutylate (2.0 g, $[\alpha]^{20}_D = -14.2°$), silver oxide (2.5 g) and hexyl iodide (4.6 g) in DMF (50 ml) was kept at 60° C. for 8 hours. The reactant was poured in ice water, precipitated substances were filtered off. Extraction was repeated with hexane.

The hexane layer obtained was washed with water and the solvent was distilled off in an evaporater. An oily substance obtained was purified by silica gel chromatography to obtain the titled compound (0.88 g).

(2) Synthesis of 4,4,4-trifluoro-3-hexyloxybutanol

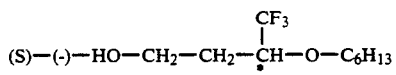

To a solution of ethyl (S)-(-)-4,4,4-trifluoro-3-hexyloxybutylate (0.88 g) in THF (20 ml) was slowly added LiAlH$_4$ (0.44 g) suspended in THF (10 ml) in ice water bath. The mixture was stirred at 0° C. for 2 hours and then additionally stirred at room temperature for 8 hours.

Aqueous hydrochloric acid solution was added to decompose the unaltered LiAlH$_4$ and solution mixture was extracted with ether. The ether layer was washed with water, dried and distilled to remove the solvent. A product obtained (0.84 g) was mainly composed of the titled compound.

EXAMPLE 2

(1) Synthesis of 4,4,4-trifluoro-3-hexyloxybutyl 4'-hydroxybenzoate

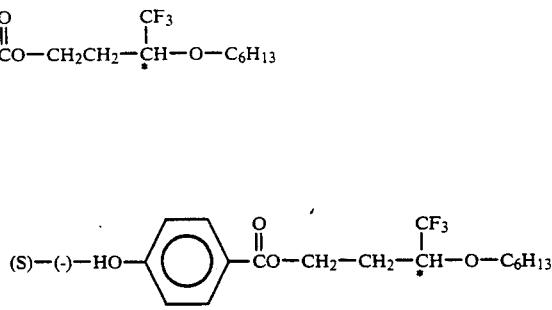

To a solution of 4,4,4-trifluoro-3-hexyloxybutanol (0.4 g) and triethyl amine (0.19 g) in methylene chloride (15 ml) was added dropwise a solution of benzyloxybenzoic acid chloride (0.48 g) in methylene chloride (5 ml). The mixture was stirred at room temperature for 12 hours.

After the reaction was over, the reactant was poured in ice water. The mixture was extracted with ether. After the ether layer was washed with water, the layer was subjected to distillation to remove the solvent and then purified by silica gel chromatography to obtain 4,4,4-trifluoro-3-hexyloxybutyl 4'-benzyloxybenzoate (0.60 g).

The product was subjected to a usual removal step of benzyl group to obtain the titled compound (0.43 g).

(2) Synthesis of 4,4,4-trifluoro-3-hexyloxybutyloxycarbonylphenyl 4-octyloxybiphenyl-4'-carboxylate

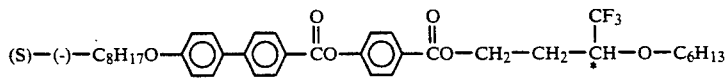

To a solution of (S)—(−)—4,4,4-trifluoro-3-hexyloxybutyl 4'-hydroxybenzoate (0.43 g) and triethyl amine (0.13 g) in methylene chloride (10 ml) was gradually added a solution of 4-octyloxybiphenyl-4'-carboxylic acid chloride (0.37 g) in methylene chloride (10 ml) while being ice cooled. The mixture was stirred at room temperature for 8 hours. After the reaction was over, the reactant was poured in ice water and then extracted with ether.

The ether layer was thoroughly washed with water, dried and distilled in order to remove the solvent. The product obtained was purified by silica gel chromatography to obtain the titled compound (0.25 g, $[\alpha]^{20}_D = -6.54°$).

The phase transition temperature and microscopic texture of the liquid crystal were determined by using Differential scanning calorimetory and polarizing microscope equipped with temperature-controlled hot stage. The phase transition temperatures are shown below:

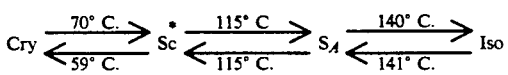

What we claim is:

1. A ferroelectric liquid crystal compound of the formula III:

7
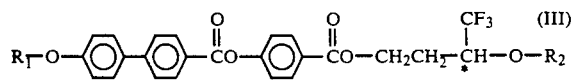
wherein $R_1$ and $R_2$ each is an alkyl group of $C_1$-$C_{18}$.
2. A ferroelectric liquid crystal compound of the following formula
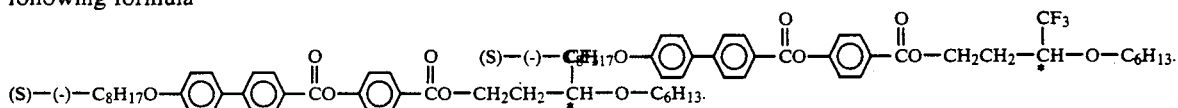
8
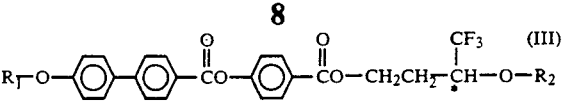
wherein $R_1$ and $R_2$ each is an alkyl group of $C_1$-$C_{18}$.
2. A ferroelectric liquid crystal compound of the following formula
* * * * *

UNITED STATES PATENT AND TRADEMARK OFFICE
CERTIFICATE OF CORRECTION

PATENT NO. : 5,096,613

DATED : March 17, 1992

INVENTOR(S) : SUZUKI et al

It is certified that error appears in the above-identified patent and that said Letters Patent is hereby corrected as shown below:

Please delete column 8, lines 1-15.

Please correct the formula in claim 2 to read as:

Signed and Sealed this

Tenth Day of August, 1993

Attest:

MICHAEL K. KIRK

Attesting Officer     Acting Commissioner of Patents and Trademarks